(12) United States Patent
Thomassian

(10) Patent No.: US 11,879,900 B2
(45) Date of Patent: *Jan. 23, 2024

(54) MASS SPECTROMETRIC QUANTITATION ASSAY FOR METABOLITES OF LEFLUNOMIDE

(71) Applicant: QUEST DIAGNOSTICS INVESTMENTS INCORPORATED, Wilmington, DE (US)

(72) Inventor: Karin O. Thomassian, Tujunga, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/745,551

(22) Filed: May 16, 2022

(65) Prior Publication Data

US 2022/0276267 A1 Sep. 1, 2022

Related U.S. Application Data

(63) Continuation of application No. 16/827,539, filed on Mar. 23, 2020, now Pat. No. 11,333,673, which is a continuation of application No. 15/730,150, filed on Oct. 11, 2017, now Pat. No. 10,598,676, which is a continuation of application No. 14/930,025, filed on Nov. 2, 2015, now Pat. No. 9,817,005, which is a continuation of application No. 13/314,093, filed on Dec. 7, 2011, now Pat. No. 9,177,766.

(60) Provisional application No. 61/428,551, filed on Dec. 30, 2010.

(51) Int. Cl.
*G01N 33/94* (2006.01)
*H01J 49/00* (2006.01)
*A61K 31/785* (2006.01)

(52) U.S. Cl.
CPC .......... *G01N 33/94* (2013.01); *A61K 31/785* (2013.01); *G01N 33/9493* (2013.01); *H01J 49/0036* (2013.01); *G01N 2560/00* (2013.01)

(58) Field of Classification Search
CPC .. G01N 33/94; G01N 33/9493; A61K 31/785; H01J 49/0036
See application file for complete search history.

(56) References Cited

U.S. PATENT DOCUMENTS

| | | |
|---|---|---|
| 5,772,874 A | 6/1998 | Quinn et al. |
| 5,795,469 A | 8/1998 | Quinn et al. |
| 5,919,368 A | 7/1999 | Quinn et al. |

(Continued)

OTHER PUBLICATIONS

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

(Continued)

*Primary Examiner* — Brian R Gordon
*Assistant Examiner* — Dwan A Gerido
(74) *Attorney, Agent, or Firm* — Foley & Lardner LLP

(57) ABSTRACT

Methods are described for determining the amount of metabolites of leflunomide in a sample. More specifically, mass spectrometric methods are described for detecting and quantifying teriflunomide in a sample.

10 Claims, 5 Drawing Sheets

(56) References Cited

U.S. PATENT DOCUMENTS

Figure 1:
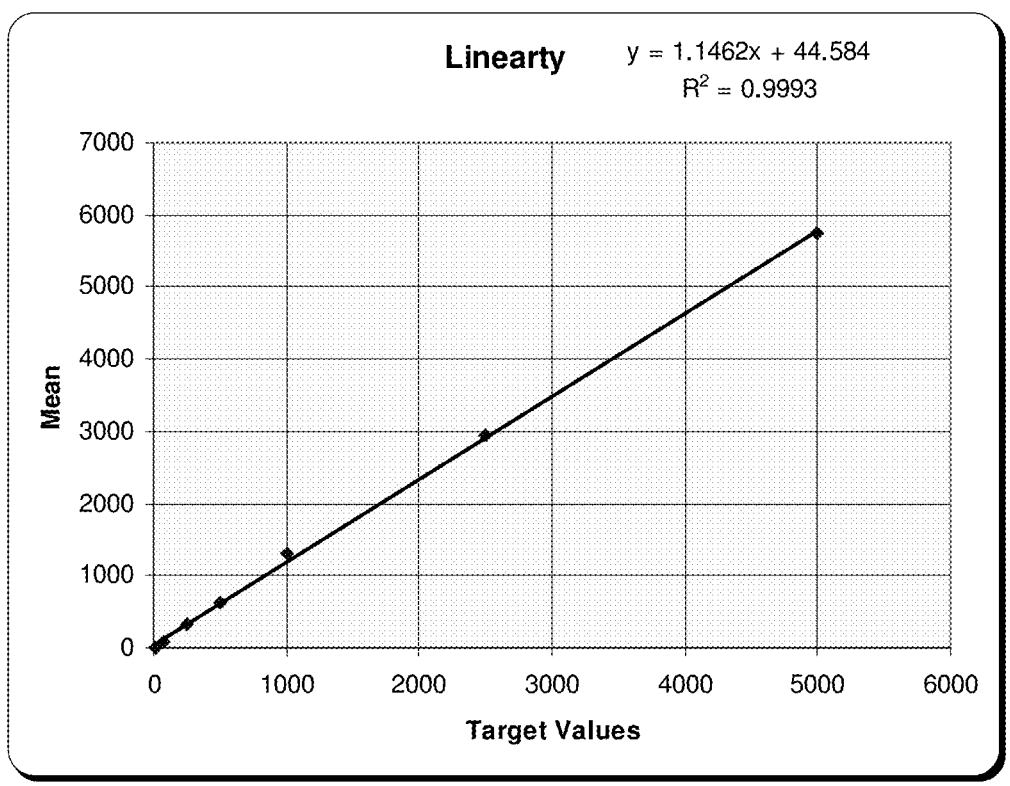

| | | | |
|---|---|---|---|
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koester |
| 9,177,766 | B2 * | 11/2015 | Thomassian ......... A61K 31/785 |
| 9,817,005 | B2 | 11/2017 | Thomassian et al. |
| 10,598,676 | B2 * | 3/2020 | Thomassian ....... G01N 33/9493 |
| 11,333,673 | B2 * | 5/2022 | Thomassian ............ A61P 43/00 |
| 2011/0111512 | A1 | 5/2011 | Bystrom et al. |

OTHER PUBLICATIONS

Chan E.C., et al., "Pharmaceutical Metabolite Profiling Using Quadrupole/Ion Mobility Spectrometry/Time-Offlight Mass Spectrometry," Rapid Communications in Mass Spectrometry, 2009, vol. 23 (3), pp. 384-394.

Chan V., et al., "Rapid Determination of the Active Leflunomide Metabolite A77 1726 in Human Plasma by High-Performance Liquid Chromatography," Journal of Chromatography B, 2004, vol. 803 (2), pp. 331-335.

Final Office Action dated Nov. 14, 2016 for U.S. Appl. No. 14/930,025, filed Nov. 2, 2015.

Final Office Action dated May 16, 2014 for U.S. Appl. No. 13/314,093, filed Dec. 7, 2011.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Non-Final Office Action dated Jan. 15, 2019 for U.S. Appl. No. 15/730,150 filed Oct. 11, 2017.

Non-Final Office Action dated Jun. 29, 2018 for U.S. Appl. No. 15/730,150, filed Oct. 11, 2017.

Non-Final Office Action dated Dec. 4, 2014 for U.S. Appl. No. 13/314,093, filed Dec. 7, 2011.

Non-Final Office Action dated Sep. 6, 2013 for U.S. Appl. No. 13/314,093, filed Dec. 7, 2011.

Non-Final Office Action dated Jan. 8, 2016 for U.S. Appl. No. 14/930,025, filed Nov. 2, 2015.

Non-Final Office Action dated Jan. 22, 2016 for U.S. Appl. No. 14/063,956, filed Oct. 25, 2013.

Non-Final Office Action dated Sep. 28, 2021 for U.S. Appl. No. 16/827,539, filed Mar. 23, 2020.

Parekh J.M., et al., "Chromatographic Separation and Sensitive Determination of Teriflunomide, an Active Metabolite of Leflunomide in Human Plasma by Liquid Chromatography-Tandem Mass Spectrometry," Journal of Chromatography B, 2010, vol. 878 (24), pp. 2217-2225.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Robb D.B., et al., "Atmospheric Pressure Photoionization: An Ionization Method for Liquid Chromatography- Mass Spectrometry," Analytical Chemistry, 2000, vol. 72 (15), pp. 3653-3659.

Seah Q.M., et al., "Oxidative Bioactivation and Toxicity of Leflunomide in Immortalized Human Hepatocytes and Kinetics of the Non-Enzymatic Conversion to Its Major Metobolite," Drug Metabolism Letters, 2008, vol. 2 (3), pp. 153-157.

Sobhani K., et al., "A Rapid and Simple High-Performance Liquid Chromatography Assay for the Leflunomide Metabolite, Teriflunomide (A77 1726), in Renal Transplant Recipients," American Journal of Clinical Pathology, 2010, vol. 133 (3), pp. 454-457.

Stafford G. C., "Instrumental Aspects of Positive and Negative Ion Chemical Ionization Mass Spectrometry," Environmental Health Perspectives, 1980, vol. 36, pp. 85-88.

Warnke C., et al., "Review of Teriflunomide and its Potential in the Treatment of Multiple Sclerosis," Journal of Neuropsychiatric Disease and Treatment, 2009, vol. 5, pp. 333-340.

WRIGHT Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography- Tandem Mass Spectrometry," Journal of Chromatography A, 1999, vol. 854, pp. 23-35.

* cited by examiner

MASS SPECTROMETRIC QUANTITATION ASSAY FOR METABOLITES OF LEFLUNOMIDE

CROSS REFERENCE TO RELATED PATENT APPLICATIONS

This application is a continuation application of U.S. application Ser. No. 16/827,539, filed Mar. 23, 2020, now U.S. Pat. No. 11,333,673, which is a continuation application of U.S. application Ser. No. 15/730,150, filed Oct. 11, 2017, now U.S. Pat. No. 10,598,676, which is a continuation application of U.S. application Ser. No. 14/930,025, filed Nov. 2, 2015, now U.S. Pat. No. 9,817,005, which is a continuation application of U.S. application Ser. No. 13/314,093, filed Dec. 7, 2011, now U.S. Pat. No. 9,177,766, which claims priority to U.S. Application Ser. No. 61/428,551, filed Dec. 30, 2010, each of which is incorporated herein by reference in its entirety.

FIELD OF THE INVENTION

The invention relates to the detection and quantitation of metabolites of leflunomide. In particular, the invention relates to methods for detection and quantitation of metabolites of leflunomide by mass spectrometry.

BACKGROUND OF THE INVENTION

The following description of the background of the invention is provided simply as an aid in understanding the invention and is not admitted to describe or constitute prior art to the invention.

Leflunomide [N-(4-trifluoromethylphenyl)-5-methyl-isoxazole-4-carboxamide] is a disease modifying antirheumatic drug (DMARD) with immunomodulatory activity. It is indicated for the treatment of active rheumatoid arthritis. Upon absorption, leflunomide is rapidly converted to the pharmacologically active metabolite, α-malononitrilamide A77 1726 [2-cyano-3-hydroxy-N-(4-trifluoromethylphenyl)-2-butenamide]. A77 1726 (also known as teriflunomide) affects de novo pyrimidine synthesis by inhibition of the enzyme dihydroorotate dehydrogenase (DHODH), thereby preferentially causing cell cycle arrest of autoimmune lymphocytes. As the conversion of leflunomide to teriflunomide in vivo is essentially complete, most pharmacokinetic studies have been conducted measuring teriflunomide and not leflunomide.

Various methods, including mass spectrometric methods, have been reported for detecting and/or quantitating A77 1726. See e.g., Chan V. et al., *J. Chromatogr. B Analyt. Technol. Biomed. Life Sci.*, 2004 Apr. 25; 803(2):331-5 (reporting a method of determining a leflunomide metabolite A77 1726 using only HPLC); Sobhani K et al., *Am. J. Clin. Pathol.* 2010 March; 133(3):454-7 (reporting a method of detecting a leflunomide metabolite using only HPLC); Seah M. S. et al., *Drug Metab. Lett.* 2008 August; 2(3):153-7 (reporting a method of detecting a leflunomide metabolite using LC and tandem MS in negative ion mode); Parekh J M et al., *J. Chromatogr. B Analyt. Technol. Biomed. Life Sci.* 2010 Aug. 15; 878(24):2217-25 (reporting a method of detecting a leflunomide metabolite using LC-MS-MS in negative ion mode); and E. C. Y. Chan et al., *Rapid Commun Mass Spectrom.* 2009 February; 23(3):384-94 (reporting a method of detecting a leflunomide metabolite using ion mobility spectrometry and time-of-flight mass spectrometry).

SUMMARY OF THE INVENTION

In one aspect, the present invention provides methods for detecting the presence or amount of teriflunomide in a sample by mass spectrometry. The methods include subjecting the sample to ionization under conditions suitable to produce one or more ions detectable by mass spectrometry; determining the amount of one or more ions by mass spectrometry; and using the amount of one or more ions to determine the presence or amount of teriflunomide in the sample.

In some embodiments, mass spectrometry comprises tandem mass spectrometry. In these embodiments, the methods include: a) ionizing the sample under conditions suitable to produce a teriflunomide precursor ion; b) fragmenting a teriflunomide precursor ion to produce one or more fragment ions; c) determining the amount of one or more ions produced in steps a) and b); and d) using the amount of the one or more ions determined in step c) to determine the presence or amount of teriflunomide in the sample. In some embodiments, a teriflunomide precursor ion with a mass to charge ratio (m/z) of 871.1±0.50 is fragmented to produce one or more fragment ions. In some related embodiments, one or more of the fragment ions are selected from the group consisting of ions with m/z of 780.6±0.50, 841.8±0.50, 940.8±0.50, 1002.5±0.50, 1040.2±0.50, 1083.9±0.50, and 1122.2±0.50. In some related embodiments, one or more of the fragment ions are selected from the group consisting of ions with m/z of 1040.2±0.50 and 1083.9±0.50.

In another embodiment, the invention provides methods for performing a cholestyramine drug elimination procedure. In some embodiments, the methods comprise administering cholestyramine to a patient; obtaining a plasma or serum sample from the patient, and detecting the level of teriflunomide in the plasma or serum sample by mass spectrometry; wherein, teriflunomide levels of 20 ng/mL or less indicate the effectiveness of the cholestyramine drug elimination procedure. Teriflunomide levels above 20 ng/mL may indicate that further administration of cholestyramine may be necessary. In these embodiments, detecting the level of teriflunomide in the patient plasma or serum may be conducted by any of the mass spectrometric procedures described herein.

In embodiments utilizing tandem mass spectrometry, tandem mass spectrometry may be conducted by any method known in the art, including for example, multiple reaction monitoring, precursor ion scanning, or product ion scanning.

The methods described herein may be capable of detecting teriflunomide at levels within the range of 2.5 ng/mL to 5000 ng/mL, inclusive; such as within the range of 10 ng/mL to 5000 μg/mL.

In some embodiments, the sample is subjected to an extraction column, such as a solid phase extraction (SPE) column, prior to ionization. In some related embodiments, SPE and mass spectrometry are conducted with on-line processing.

In some embodiments, the sample is subjected to an analytical column, such as a high performance liquid chromatography (HPLC) column, prior to ionization. In some related embodiments, HPLC and mass spectrometry are conducted with on-line processing.

In some embodiments, the methods may be used to determine the presence or amount of teriflunomide in a biological sample; such as plasma or serum. In some related embodiments, a biological sample is processed by one or more steps to generate a processed sample, which may then be subjected to mass spectrometric analysis. In some embodiments, the one or more processing steps comprise one or more purification steps, such as protein precipitation, filtration, liquid-liquid extraction, solid phase extraction, liquid chromatography, any immunopurification process, or the like, and any combination thereof.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain embodiments, teriflunomide is measured using ESI in positive ion mode.

In preferred embodiments, a separately detectable internal standard is provided in the sample, the amount of which is also determined in the sample. In these embodiments, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample.

In other embodiments, the amount of the teriflunomide in a sample may be determined by comparison to one or more external reference standards. Exemplary external reference standards include blank plasma or serum spiked with teriflunomide or an isotopically labeled variant thereof.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest Immunopurification can be performed using any of the immunopurification methods well known in the art. Often the immunopurification procedure utilizes antibodies bound, conjugated or otherwise attached to a solid support, for example a column, well, tube, gel, capsule, particle or the like Immunopurification as used herein includes without limitation procedures often referred to in the art as immunoprecipitation, as well as procedures often referred to in the art as affinity chromatography.

As used herein, the term "immunoparticle" refers to a capsule, bead, gel particle or the like that has antibodies bound, conjugated or otherwise attached to its surface (either on and/or in the particle). In certain embodiments utilizing immunopurification, immunoparticles comprise sepharose or agarose beads. In alternative embodiments utilizing immunopurification, immunoparticles comprise glass, plastic or silica beads, or silica gel.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In some embodiments, the sample comprises a body fluid sample; preferably plasma or serum.

As used herein, the term "solid phase extraction" or "SPE" refers to a process in which a chemical mixture is separated into components as a result of an affinity of components dissolved or suspended in a solution (i.e., mobile phase) for a solid through or around which the solution is passed (i.e., solid phase). SPE, as used herein, is distinct from immunopurification in that the affinity of components in the mobile phase to the solid phase is the result of a chemical or physical interaction, rather than an immunoaffinity. In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr A 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar Many references are available for assisting in determining when fluid flow is laminar or turbulent (e.g., Turbulent Flow Analysis: Measurement and Prediction, P. S. Bernard & J. M. Wallace, John Wiley & Sons, Inc., (2000); An Introduction to Turbulent Flow, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 μm in diameter.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autos ampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e g ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor.

This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., Anal. Chem. 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1 shows a plot of the linearity of quantitation of teriflunomide in spiked mimic serum standards. Details are described in Example 4.

FIG. 2 shows a plot showing the correlation of expected and detected teriflunomide concentrations in forty spiked serum samples. Details are described in Example 7.

FIG. 3 shows a plot showing the correlation of expected and detected teriflunomide concentrations in spiked heparin plasma samples. Details are described in Example 8.

FIG. 4 shows a plot showing the correlation of expected and detected teriflunomide concentrations in spiked acid-citrate-dextrose samples. Details are described in Example 8.

FIG. 5 shows a plot showing the correlation of expected and detected teriflunomide concentrations in spiked EDTA plasma samples. Details are described in Example 8.

DETAILED DESCRIPTION OF THE INVENTION

Methods are described for measuring the amount of teriflunomide in a sample. More specifically, mass spectrometric methods are described for detecting and/or quantifying teriflunomide in a biological sample, such as human plasma or serum. The methods may utilize liquid chromatography followed by tandem mass spectrometry to quantitate teriflunomide in the sample.

Mean steady state plasma concentrations of teriflunomide from patients on daily dosages of 5, 10, or 25 mg of leflunomide may be expected to be about 8800 ng/mL, 18,000 ng/mL, and 63,000 ng/mL, respectively. For patients who have been prescribed leflunomide, quantitation of teriflunomide in their plasma may provide a means to confirm compliance with the prescribed dosages, or may provide a means to determine if adjustments to prescribed dosages may be necessary.

Further, it is recommended that women of childbearing potential who discontinue leflunomide therapy undergo a cholestyramine drug elimination procedure. Such procedures include administration of cholestyramine for a plurality of consecutive or non-consecutive days, followed by verification that plasma levels of teriflunomide are less than 20 ng/mL at least 14 days apart. Thus, methods of the present invention provide a means of confirming the effectiveness of a cholestyramine drug elimination procedure; that is, methods of the present invention may be used to confirm that a sample contains less than 20 ng/mL of teriflunomide.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In some embodiments, preferred samples may be obtained from female humans of childbearing potential. In embodiments where the sample comprises a biological sample, the methods may be used to determine the amount of leflunomide metabolite in the sample when the sample was obtained from the biological source (i.e., the amount of endogenous leflunomide metabolite in the sample).

The present invention also contemplates kits for a teriflunomide quantitation assay. A kit for a teriflunomide quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a teriflunomide quantitation assay.

Calibration and QC pools for use in embodiments of the present invention are preferably prepared using a matrix similar to the intended sample matrix, provided that teriflunomide is essentially absent.

Sample Preparation for Mass Spectrometric Analysis

In preparation for mass spectrometric analysis, teriflunomide may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art. For example, Polson et al., Journal of Chromatography B 2003, 785:263-275, describes protein precipitation techniques suitable for use in methods of the present invention. Protein precipitation may be used to remove most of the protein from the sample leaving teriflunomide in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to additional purification methods, such as liquid chromatography, and subsequent mass spectrometry analysis. In certain embodiments, the use of protein precipitation, such as for example, acetonitrile protein precipitation, may obviate the need for TFLC or other on-line extraction prior to mass spectrometry or high performance liquid chromatography (HPLC) and mass spectrometry.

Another method of sample purification that may be used prior to mass spectrometry is liquid chromatography (LC). Certain methods of liquid chromatography, including high performance liquid chromatography (HPLC), rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with teriflunomide. The chromatographic column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded, cyano bonded, or biphenyl bonded surface. Alkyl bonded surfaces may include C-4, C-8, C-12, or C-18 bonded alkyl groups. In preferred embodiments, the column is a biphenyl column. The chromatographic column includes an inlet port for receiving a sample and an outlet port for discharging an effluent that includes the fractionated sample. The sample may be supplied to the inlet port directly, or from a SPE column, such as an on-line extraction column or a TFLC column. In some embodiments, an on-line guard cartridge may be used ahead of the HPLC column to remove particulates and phospholipids in the samples prior to the samples reaching the HPLC column. In some embodiments, guard cartridge may be a biphenyl guard cartridge.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a biphenyl column chromatographic system. In certain preferred embodiments, a biphenyl analytical column (e.g., a Pinnacle DB Biphenyl analytical column from Restek Inc. (5 μm particle size, 50×2.1 mm), or equivalent) is used. In certain preferred embodiments, HPLC is performed using HPLC Grade 0.1% aqueous formic acid as solvent A, and 0.1% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of teriflunomide prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge may be accomplished with a large particle size (50 μm) packed column. Sample eluted off of this column is then transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, teriflunomide may be ionized by any method known to the skilled artisan. Mass spectrometry is performed using a mass spectrometer, which includes an ion source for ionizing the fractionated sample and creating charged molecules for further analysis. For example, ionization of the sample may be performed by electron ionization, chemical ionization, electrospray ionization (ESI), photon ionization, atmospheric pressure chemical ionization (APCI), photoionization, atmospheric pressure photoionization (APPI), laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Teriflunomide may be ionized in positive or negative mode. In some embodiments, teriflunomide is ionized by ESI in positive mode.

In mass spectrometry techniques generally, after the sample has been ionized, the positively or negatively charged ions thereby created may be analyzed to determine a mass to charge ratio (m/z). Suitable analyzers for determining m/z include quadrupole analyzers, ion traps analyzers, and time-of-flight analyzers. Exemplary ion trap methods are described in Bartolucci, et al., *Rapid Commun. Mass Spectrom.* 2000, 14:967-73.

According to some methods of the present invention, high resolution/high accuracy mass spectrometry is used for quantitation of teriflunomide. That is, mass spectrometry is conducted with a mass spectrometer capable of exhibiting a resolving power (FWHM) of at least 10,000, with accuracy of about 50 ppm or less for the ions of interest; preferably the mass spectrometer exhibits a resolving power (FWHM) of 20,000 or better and accuracy of about 20 ppm or less; such as a resolving power (FWHM) of 25,000 or better and accuracy of about 5 ppm or less; such as a resolving power (FWHM) of 25,000 or better and accuracy of about 3 ppm or less. Three exemplary mass spectrometers capable of exhibiting the requisite level of performance for teriflunomide ions are those which include orbitrap mass analyzers, certain TOF mass analyzers, or Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring carbon containing molecules will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron 1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2 (difference of 1 amu/charge state of 5). High resolution/high accuracy mass spectrometers are capable of discerning between isotopic forms of highly multiply charged ions (such as ions with charges of ±4, ±5, ±6, ±7, ±8, ±9, or higher).

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z and relative abundances of two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks or averaging the response from multiple peaks.

In mass spectrometry techniques generally, ions may be detected using several detection modes. For example, selected ions may be detected, i.e. using a selective ion monitoring mode (SIM), or alternatively, mass transitions resulting from collision activated dissociation (CAD), e.g., multiple reaction monitoring (MRM) or selected reaction monitoring (SRM). CAD is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy. Alternatively, neutral loss may be monitored.

In some embodiments, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the specificity of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of teriflunomide. Methods of generating and using such standard curves are well known in the art and one of ordinary skill is capable of selecting an appropriate internal standard. For example, one or more forms of an isotopically labeled molecule with a similar m/z as teriflunomide may be used as internal standards. In some embodiments described herein, an exemplary internal standard is an isotopically labeled diazepam, although numerous other compounds (isotopically labeled or otherwise) may be used. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques.

Examples of suitable labels include deuterium ($^{2}H$), $^{13}C$, and $^{15}N$. One or more isotopic labels can be incorporated at one or more positions in the molecule and one or more kinds of isotopic labels can be used on the same isotopically labeled molecule.

One or more steps of the methods may be performed using automated machines.

In certain embodiments, one or more purification steps are performed on-line, and more preferably all of the purification and mass spectrometry steps may be performed in an on-line fashion.

In particularly preferred embodiments, teriflunomide in a sample is detected and/or quantified using MS/MS as follows. Samples are preferably subjected to SPE, then subjected to liquid chromatography, preferably HPLC; the flow of liquid solvent from a chromatographic column enters the heated nebulizer interface of an MS/MS analyzer; and the solvent/analyte mixture is converted to vapor in the heated charged tubing of the interface. During these processes, the analyte (i.e., teriflunomide) is analyzed. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of teriflunomide. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of teriflunomide are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of teriflunomide that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of teriflunomide. As described above, the relative abundance of a given ion may be converted into an absolute amount of the original analyte using calibration standard curves based on peaks of one or more ions of an internal or external molecular standard.

The following Examples serve to illustrate the invention. These Examples are in no way intended to limit the scope of the methods.

EXAMPLES

Example 1: Sample Preparation

Calibrator samples were prepared at eight different concentrations of teriflunomide in drug free serum (obtained from BioRad). The serum standards were prepared at concentrations of 10 ng/mL, 25 ng/mL, 75 ng/mL, 250 ng/mL, 500 ng/mL, 1000 ng/mL, 2500 ng/mL, and 5000 ng/mL. Control samples were prepared at two different concentrations of teriflunomide in drug free serum (at ~100 ng/mL and ~750 ng/mL).

Patient samples (human serum), calibrator samples, controls, and blanks were prepared for analysis by acetonitrile protein precipitation as follows.

100 μL of each sample was transferred into a 1.5 ml plastic vial. 20 μL of internal standard solution (1000 mg/mL diazepam-$d_5$ in methanol) and 200 μL of acetonitrile were added to each vial, and the resulting mixture vortexed for about 30 seconds. The vortexed samples were incubated at room temperature for about 15 minutes and centrifuged for about 20 minutes at about 5000 rpm. For any sample that was still cloudy, the supernatant was removed and centrifuged again for about an additional 2 minutes at about 2000 rpm, and the resulting supernatant removed again.

200 μL of the resulting supernatants from each sample was transferred to autosampler injection vials for LC-MS/MS analysis as described below.

Example 2: Enrichment of Teriflunomide Using Liquid Chromatography

Injection of 2 μL of each sample was performed with a CTC Analytics HTS-PAL system using Analyst 1.5.1 or newer software.

The injected samples were first passed through an on-line Restek Pinnacle DB Biphenyl guard cartridge (5 μm, 10×2.1 mm) prior to introduction into a Restek Pinnacle DP Biphenyl analytical column (5 μm, 50×2.1 mm). An HPLC gradient was applied to the analytical column, to separate teriflunomide from other analytes contained in the sample. Mobile phase A was 0.1% formic acid in HPLC grade water and mobile phase B was 0.1% formic acid in acetonitrile. The HPLC gradient started with 90% mobile phase A for 0.5 minutes, ramped to 80% mobile phase A in approximately 0.5 minutes, ramped again to 70% mobile phase A in approximately 0.5 minutes, ramped again to 10% mobile phase A in approximately 0.3 minutes, and finally ramped back to 90% mobile phase A in approximately 0.2 minutes, for a total assay run time of approximately 2 minutes.

The separated samples are then subjected to MS/MS for quantitation of teriflunomide.

Example 3: Detection and Quantitation of Teriflunomide by Tandem MS

MS/MS was performed using an Applied Biosystems API4000. Liquid solvent/analyte exiting the analytical column flowed to the TurboSpray (ESI) interface of the MS/MS analyzer. The solvent/analyte mixture was converted to vapor in the heated tubing of the interface, and the resulting vapor was ionized by ESI in positive ion mode.

Teriflunomide ions passed to the first quadrupole (Q1), which selected ions with a m/z of 271.3±0.50. Ions entering quadrupole 2 (Q2) collided with nitrogen gas (at a collision cell energy of 17-18 V) to generate ion fragments, which were passed to quadrupole 3 (Q3) for further selection. Similarly, diazepam-$d_5$ (internal standard) ions with m/z of 290.2±0.50 were selected at Q1, with fragments generated in Q2 and further selected in Q3. The following mass transitions were monitored for teriflunomide and diazepam-$d_5$.

TABLE 1

| Mass Transitions Observed for Teriflunomide and Diazepam-$d_5$ (Positive Polarity) | | |
|---|---|---|
| Analyte | Precursor Ion (m/z) | Productions (m/z) |
| Teruflunomide | 271.3 ± 0.50 | 162.1 ± 0.50 (Quantifier) |
|  |  | 142.2 ± 0.50 (Qualifier) |
| Diazepam-$d_5$ | 290.2 ± 0.50 | 198.1 ± 0.50 |

Of the observed teriflunomide transitions, one was were monitored in MRM mode for quantitative analysis (the precursor ion with m/z of 271.3±0.50 to the fragment ion with m/z of 162.1±0.50) and one was monitored as a qualifying transition to confirm the identity of the observed ions (the precursor ion with m/z of 271.3±0.50 to the fragment ion with m/z of 142.2±0.50).

The ratio of the signals of the quantifying transition and qualifying transition were evaluated for each sample. Observed ion ratios from patient samples that are within 20% of the average ratios from the calibrator samples were considered to confirm the source of ions in the patient samples.

While this second transition was used for qualification of the observed transitions, it could have been used to supplement the quantitative data collected by monitoring the first transition. In fact, additional product ions may be selected to replace or augment either of the monitored transitions.

Example 4: Intra-assay and Inter-assay Precision

The two quality control (QC) pools prepared in Example 1 (with teriflunomide concentrations at ~100 ng/mL and ~750 ng/mL) were analyzed to determine intra-assay and inter-assay precision and accuracy.

Five aliquots from each of the two QC pools were analyzed in a five assays to determine the reproducibility (Overall CV (%)) across assays. The following values were determined:

TABLE 2

| Intra-Assay and Inter-Assay Variation | | | | | |
|---|---|---|---|---|---|
|  | Run 1 (ng/mL) | Run 2 (ng/mL) | Run 3 (ng/mL) | Run 4 (ng/mL) | Run 5 (ng/mL) |
| Level 1 | | | | | |
| 1 | 109.00 | 115.00 | 130.00 | 112.00 | 102.00 |
| 2 | 102.00 | 106.00 | 113.00 | 102.00 | 106.00 |
| 3 | 103.00 | 131.00 | 127.00 | 106.00 | 125.00 |
| 4 | 93.40 | 103.00 | 87.50 | 109.00 | 107.00 |
| 5 | 121.00 | 120.00 | 119.00 | 122.00 | 119.00 |
| Count | 5 | 5 | 5 | 5 | 5 |
| Average | 105.68 | 115.00 | 115.30 | 110.20 | 111.80 |
| In Run SD | 10.21 | 11.25 | 16.92 | 7.56 | 9.73 |
| Level 2 | | | | | |
| 1 | 708.00 | 722.00 | 821.00 | 779.00 | 807.00 |
| 2 | 755.00 | 749.00 | 753.00 | 761.00 | 765.00 |
| 3 | 793.00 | 849.00 | 814.00 | 844.00 | 810.00 |

TABLE 2-continued

| Intra-Assay and Inter-Assay Variation | | | | | |
|---|---|---|---|---|---|
| 4 | 798.00 | 826.00 | 815.00 | 776.00 | 728.00 |
| 5 | 779.00 | 754.00 | 673.00 | 807.00 | 741.00 |
| Count | 5 | 5 | 5 | 5 | 5 |
| Average | 766.60 | 780.00 | 775.20 | 793.40 | 770.20 |
| In Run SD | 36.76 | 54.49 | 63.49 | 32.81 | 37.41 |

| Summary | Level 1 | Level 2 |
|---|---|---|
| Count | 25 | 25 |
| Grand Mean | 111.60 | 777.08 |
| Pooled WR SD | 11.57 | 46.54 |
| Pooled WR CV | 10.36% | 5.99% |
| Overall SD | 11.16 | 43.54 |
| Overall CV | 10.00% | 5.60% |
| Sigma Overall | 3.00 | 5.35 |
| Precision >=3.0 sigma? | YES | YES |

Example 5: Assay Reportable Range and Linearity

To establish the linearity of teriflunomide detection in the assay, seven standards at concentrations ranging from 10 ng/mL to 5000 ng/mL (prepared in Example 1) were analyzed in duplicate. Results of these analyses are shown in Table 3.

TABLE 3

| Linearity | | | |
|---|---|---|---|
| Target Values (ng/mL) | First Reading (ng/mL) | Second reading (ng/mL) | Mean (ng/mL) |
| 10 | 4.40 | 8.90 | 6.65 |
| 75 | 89.30 | 67.30 | 78.3 |
| 250 | 306.00 | 372.00 | 339 |
| 500 | 538.00 | 697.00 | 617.5 |
| 1000 | 1140.00 | 1450.00 | 1295 |
| 2500 | 2380.00 | 3480.00 | 2930 |
| 5000 | 4870.00 | 6620.00 | 5745 |

A quadratic regression from the two runs yielded a $R^2$ value of 0.9993. A graph showing the linearity of the data is shown in FIG. 1. The assay was shown to be linear up to 5000 ng/mL, giving a reportable range of 10 to 5000 ng/mL.

Example 6: Analytical Sensitivity: Limit of Detection (LOD), Lower Limit of Detection (LLD), and Lower Limit of Quantitation (LOQ)

The LOD is the point at which a value is beyond the uncertainty associated with its measurement and is defined arbitrarily as two times the standard deviation (SD) of the mean from the Zero concentration. The analytical sensitivity is the ability of an analytical method to differentiate and quantify an analyte in the presence of other compounds in the sample. For selectivity, blank (diluent) samples were obtained, tested for interference, and selectivity ensured at the lower limit of quantification. Diluent (blank) samples was run in 20 replicates each and the resulting values statistically analyzed to determine the LOD.

The analytical sensitivity of the assay was determined as the lower limit of detection (LLD). The LLD and LOQ were determined by testing 20 replicates of sample diluent and calculating the Mean+4SD, while LOQ was mean+10SD. Data from these analyses is presented in Table 4, below. As seen in Table 4, the statistical LOQ was 2.24 ng/mL, which is lower than the concentration of the lowest standard sample tested (at 10 ng/mL).

TABLE 4

| Analyses of blank samples for LOD, LLD, and LOQ | |
|---|---|
| REPLICATE # | PK AREA |
| 1 | 49400.00 |
| 2 | 50600.00 |
| 3 | 46500.00 |
| 4 | 43600.00 |
| 5 | 49800.00 |
| 6 | 49700.00 |
| 7 | 45800.00 |
| 8 | 44600.00 |
| 9 | 42800.00 |
| 10 | 43500.00 |
| 11 | 47700.00 |
| 12 | 45000.00 |
| 13 | 48500.00 |
| 14 | 47900.00 |
| 15 | 45800.00 |
| 16 | 49200.00 |
| 17 | 47000.00 |
| 18 | 49100.00 |
| 19 | 44500.00 |
| 20 | 50300.00 |
| MEAN | 47065 |
| STDEV | 2429 |
| LOD (STDEV × 4) | 9718 |
| STDEV × 10 | 24295 |
| Variable A = MEAN + (STDEV × 10) | 49494 |
| Variable B = PK AREA (STD 1) | 110000.00 |
| LOQ BASED ON AREA | =(A × 5)/ B |
| LOQ BASED ON AREA (ng/mL) | 2.249748173 |

Example 7: Assay Accuracy: Comparison of Clinically Defined Samples

A study of the accuracy of teriflunomide quantitation was carried out by testing forty spiked samples according to the procedures described in Examples 1-3, and the amounts of detected teriflunomide compared to the spiked values. The results of these analyses are shown in Table 5, below.

TABLE 5

| Detection of Teriflunomide in Spiked Serum Samples | | |
|---|---|---|
| Sample | Spiked Teriflunomide (ng/mL) | Detected Teriflunomide (ng/mL) | Recovery (%) |
| 1 | 5000 | 5410 | 108.20 |
| 2 | 5000 | 5120 | 102.40 |
| 3 | 500 | 513 | 102.60 |
| 4 | 500 | 497 | 99.40 |
| 5 | 500 | 561 | 112.20 |
| 6 | 1000 | 1070 | 107.00 |
| 7 | 1000 | 1010 | 101.00 |
| 8 | 1000 | 1010 | 101.00 |
| 9 | 1500 | 1430 | 95.33 |
| 10 | 1500 | 1670 | 111.33 |
| 11 | 1500 | 1410 | 94.00 |
| 12 | 250 | 237 | 96.80 |
| 13 | 250 | 242 | 89.60 |
| 14 | 250 | 224 | 89.60 |
| 15 | 500 | 477 | 96.60 |
| 16 | 500 | 483 | 111.40 |
| 17 | 500 | 557 | 111.40 |
| 18 | 750 | 651 | 100.53 |
| 19 | 750 | 754 | 98.80 |
| 20 | 750 | 741 | 98.80 |
| 21 | 178.5 | 124 | 77.31 |
| 22 | 178.5 | 138 | 87.39 |
| 23 | 178.5 | 156 | 87.39 |
| 24 | 357 | 320 | 89.64 |
| 25 | 357 | 309 | 86.55 |
| 26 | 357 | 341 | 95.52 |

TABLE 5-continued

Detection of Teriflunomide in Spiked Serum Samples

| Sample | Spiked Teriflunomide (ng/mL) | Detected Teriflunomide (ng/mL) | Recovery (%) |
|---|---|---|---|
| 27 | 100 | 115 | 115.00 |
| 28 | 100 | 98 | 98.00 |
| 29 | 100 | 85.7 | 85.70 |
| 30 | 100 | 83 | 83.00 |
| 31 | 100 | 117 | 117.00 |
| 32 | 750 | 779 | 103.87 |
| 33 | 750 | 754 | 100.53 |
| 34 | 750 | 673 | 89.73 |
| 35 | 750 | 807 | 107.60 |
| 36 | 750 | 741 | 98.80 |
| 37 | 850 | 889 | 104.59 |
| 38 | 850 | 826 | 97.18 |
| 39 | 850 | 818 | 96.24 |
| 40 | 850 | 841 | 98.94 |

Figure 2:
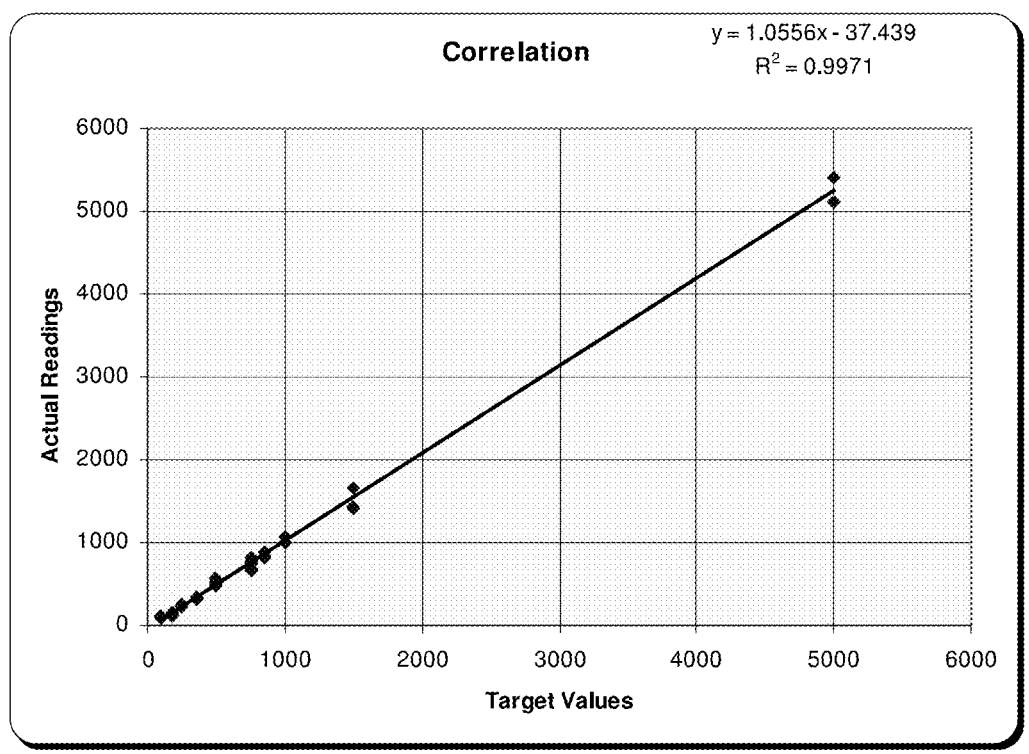

The results of the expected and detected values from the forty spiked samples correlated with an $R^2=0.9971$ and an intercept of −37.4. A graph showing the correlation of the data is shown in FIG. 2. Additionally, the mean recovery was 98.7%.

Example 8: Comparison of Specimen Types

Figure 3:
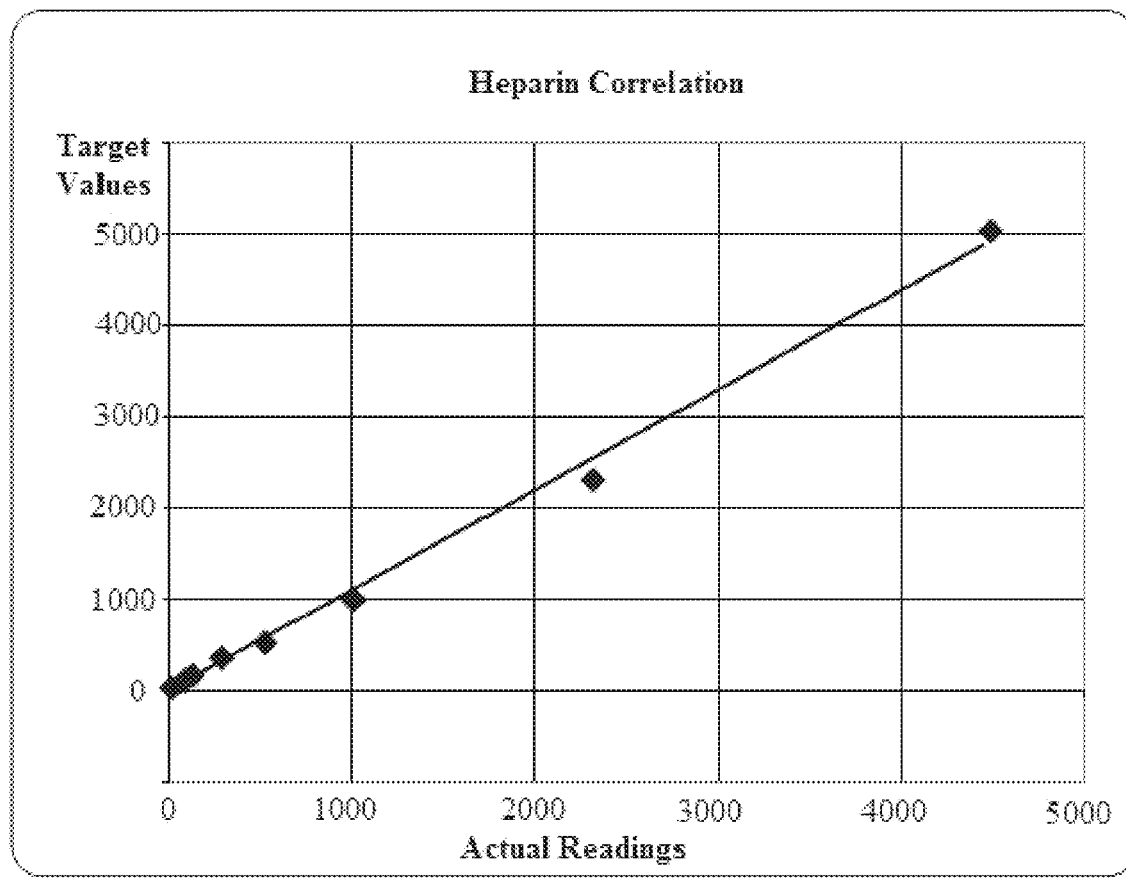
Figure 4:
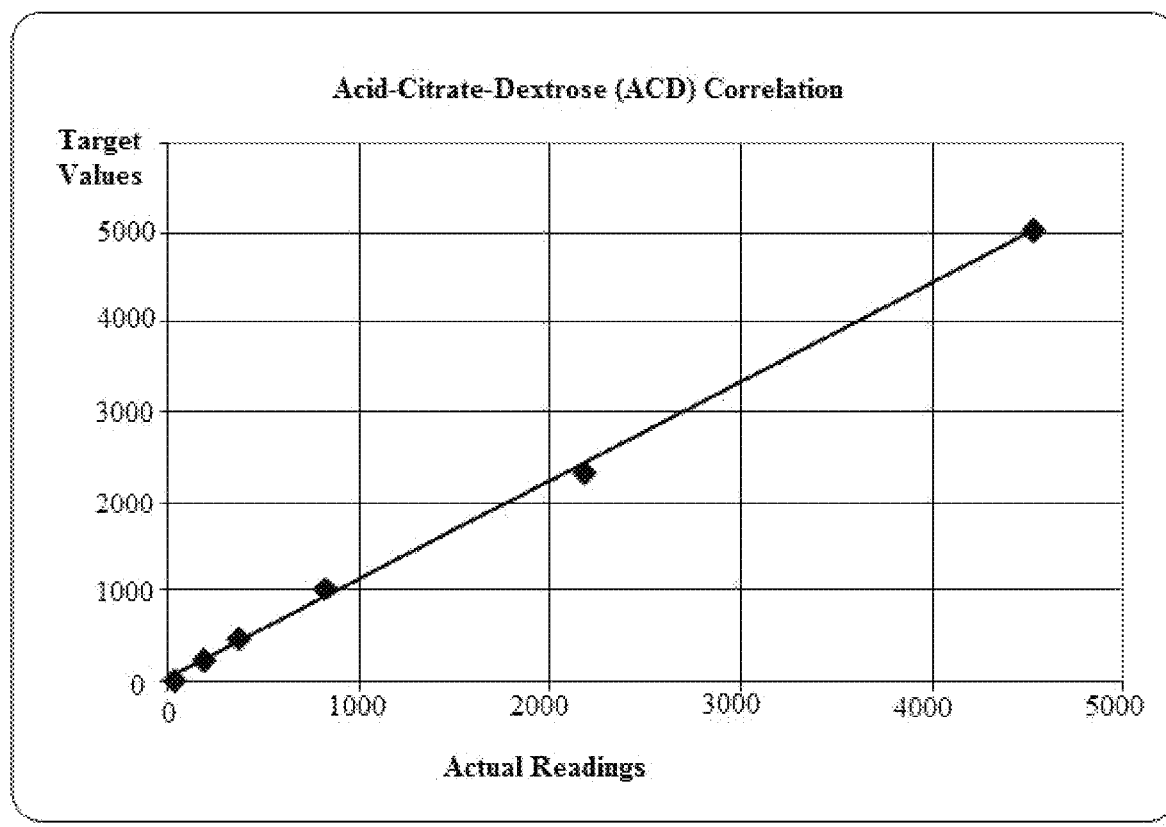
Figure 5:
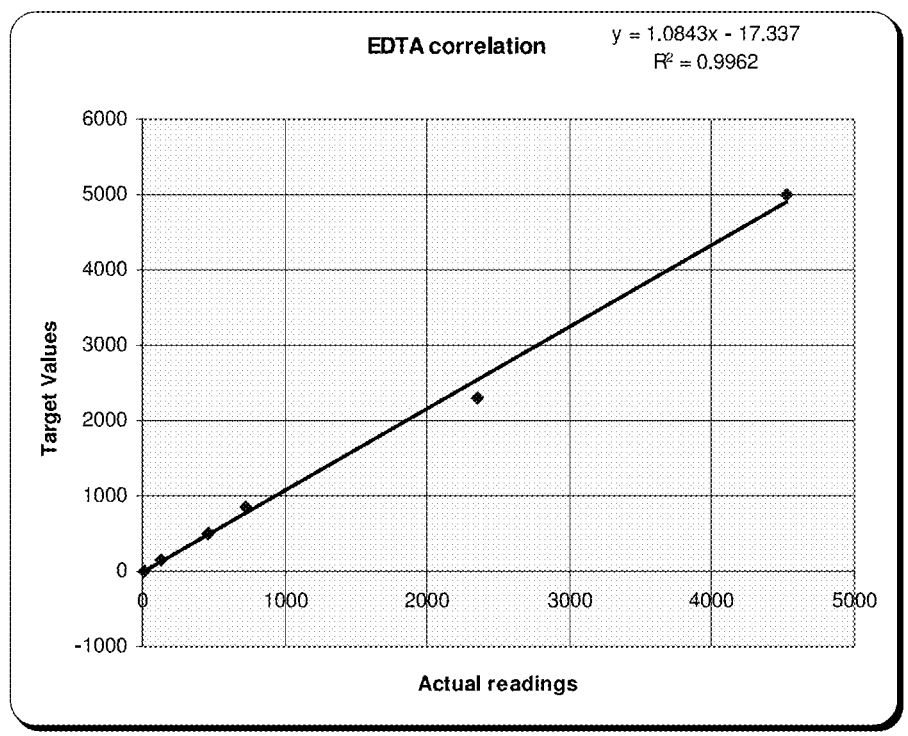

Correlation studies similar to that described in Example 6 were performed on different specimen types (Heparin, Acid-Citrate-Dextrose (or ACD), and EDTA plasmas) to determine the affect of these different sample types on quantitation of teriflunomide. For heparin plasma, eight spiked standards at concentrations from about 10-5000 ng/mL were analyzed. For ACD and EDTA plasmas, six spiked standards at concentrations from about 10-5000 ng/mL were analyzed. Results of these analyses are shown in Tables 6-8, and the correlations plotted in FIGS. 3-5.

TABLE 6

Detection of Teriflunomide in Spiked Heparin Plasma Samples

| Sample | Spiked Teriflunomide (ng/mL) | Detected Teriflunomide (ng/mL) | Recovery (%) |
|---|---|---|---|
| HEP1 | 5000 | 4460 | 89.20 |
| HEP2 | 2300 | 2330 | 101.30 |
| HEP3 | 1000 | 982 | 98.20 |
| HEP4 | 500 | 514 | 102.80 |
| HEP5 | 250 | 256 | 102.40 |
| HEP6 | 60 | 56.5 | 94.17 |
| HEP7 | 30 | 34.9 | 116.33 |
| HEP8 | 10 | 12.5 | 125.00 |

TABLE 7

Detection of Teriflunomide in Spiked ACD Plasma Samples

| Sample | Spiked Teriflunomide (ng/mL) | Detected Teriflunomide (ng/mL) | Recovery (%) |
|---|---|---|---|
| ACD1 | 5000 | 4510 | 90.20 |
| ACD2 | 2300 | 2130 | 92.61 |
| ACD3 | 1000 | 851 | 85.10 |
| ACD4 | 400 | 352 | 88.00 |
| ACD5 | 200 | 168 | 84.00 |
| ACD8 | 10 | 10.8 | 108.00 |

TABLE 8

Detection of Teriflunomide in Spiked EDTA Plasma Samples

| Sample | Spiked Teriflunomide (ng/mL) | Detected Teriflunomide (ng/mL) | Recovery (%) |
|---|---|---|---|
| EDTA1 | 5000 | 4530 | 90.60 |
| EDTA2 | 2300 | 2350 | 102.17 |
| EDTA3 | 850 | 734 | 86.35 |
| EDTA4 | 500 | 458 | 91.60 |
| EDTA5 | 150 | 138 | 92.00 |
| EDTA6 | 10 | 11 | 110.00 |

The observed correlations were acceptable for all sample types.

Example 9: Interference Studies

Hemolysis Interference: The effects of hemolysis in the assay were evaluated by spiking various levels of hemoglobin into the 175 ng/mL teriflunomide in drug-free serum to mimic various degrees of hemolysis (low, medium, and high). All samples were analyzed in duplicate. The results of these analyses are shown in Table 9.

TABLE 9

Hemolysis Interference Studies for Teriflunomide

| Sample | Expected (ng/mL) | First Reading (ng/mL) | Second Reading (ng/mL) | Average (ng/mL) | Recovery (%) |
|---|---|---|---|---|---|
| Neat | 175 | 175 | 175 | 175 | |
| Hem (Low) | 175 | 170 | 171 | 170.5 | 97.4 |
| Hem (Mid) | 175 | 184 | 179 | 181.5 | 103.7 |
| Hem (High) | 175 | 142 | 139 | 140.5 | 80.3 |

The recovery for all hemolytic samples were within the range of acceptable results (80%-110%).

Lipid Interference: The effects of lipids in the assay were evaluated by spiking various levels of triglycerides into the 175 ng/mL teriflunomide in drug-free serum to mimic various degrees of lipemic samples (low, medium, and high). All samples were analyzed in duplicate. The results of these analyses are shown in Table 10.

TABLE 10

Lipid Interference Studies for Teriflunomide

| Sample | Expected (ng/mL) | First Reading (ng/mL) | Second Reading (ng/mL) | Average (ng/mL) | Recovery (%) |
|---|---|---|---|---|---|
| Neat | 175 | 175 | 175 | 175 | |
| Trig (Low) | 175 | 160 | 155 | 157.5 | 90.0 |
| Trig (Mid) | 175 | 146 | 146 | 146 | 83.4 |
| Trig (High) | 175 | 125 | 114.5 | 119.5 | 68.3 |

The recovery for grossly lipemic samples was not acceptable. The recovery was outside of the range of acceptable results (80%410%).

Bilirubin Interference: The effects of bilirubin in the assay were evaluated by spiking various levels bilirubin into the 175 ng/mL teriflunomide in drug-free serum to mimic various degrees of icteric samples (low, medium, and high). All samples were analyzed in duplicate. The results of these analyses are shown in Table 11.

TABLE 13

Bilirubin Interference Studies for Teriflunomide

| Sample | Expected (ng/mL) | First Reading (ng/mL) | Second Reading (ng/mL) | Average (ng/mL) | Recovery (%) |
|---|---|---|---|---|---|
| Neat | 175 | 175 | 175 | 175 | |
| Bilirubin (Low) | 175 | 151 | 145 | 148 | 84.6 |
| Bilirubin (Mid) | 175 | 154 | 142 | 148 | 84.6 |
| Bilirubin (High) | 175 | 128 | 138 | 133 | 76.0 |

The recovery for grossly icteric samples was not acceptable. The recovery was outside of the range of acceptable results (80%410%).

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of teriflunomide in a sample by mass spectrometry, said method comprising:
    a. adding an internal standard to the sample;
    b. purifying the sample by high turbulence liquid chromatography (HTLC);
    c. ionizing the sample to produce one or more teriflunomide ions detectable by mass spectrometry;
    d. determining the amount of the one or more teriflunomide ions by mass spectrometry; and
    e. using the amount of the one or more ions determined in step (d) to determine the amount of teriflunomide in the sample; and
    f. confirming the identity of teriflunomide by detecting a qualifier ion with m/z of 142.2±0.50.

2. The method of claim 1, wherein said mass spectrometry is tandem mass spectrometry.

3. The method of claim 2, wherein tandem mass spectrometry is conducted by multiple reaction monitoring, precursor ion scanning, or product ion scanning.

4. The method of claim 1, wherein the amount of a fragment ion with m/z of 162.1±0.50 is used to determine the amount of teriflunomide in a sample.

5. The method of claim 1, wherein ionization is conducted with an electrospray ionization (ESI) source.

6. The method of claim 1, wherein ionization is conducted with an atmospheric pressure chemical ionization (APCI) source.

7. The method of claim 1, wherein the sample is subjected to protein precipitation prior to mass spectrometric ionization.

8. The method of claim 1, wherein the sample is a biological sample.

9. The method of claim 8, wherein the biological sample is plasma.

10. The method of claim 8, wherein the biological sample is serum.

* * * * *